US005654451A

United States Patent [19]

Kari

[11] Patent Number: 5,654,451
[45] Date of Patent: Aug. 5, 1997

[54] AMINO ACIDS AND PEPTIDES HAVING MODIFIED C-TERMINALS AND MODIFIED N-TERMINALS

[75] Inventor: U. Prasad Kari, Lansdale, Pa.

[73] Assignee: Magainin Pharmaceuticals Inc., Plymouth Meeting, Pa.

[21] Appl. No.: 430,462

[22] Filed: Apr. 28, 1995

Related U.S. Application Data

[63] Continuation-in-part of Ser. No. 199,553, Feb. 22, 1994, abandoned, which is a continuation-in-part of Ser. No. 4,313, Jan. 14, 1993, abandoned.

[51] Int. Cl.$^6$ ................................................ C07C 233/05
[52] U.S. Cl. .................. 554/35; 530/300; 554/36; 554/51; 554/53; 564/153; 564/157; 564/159; 564/164
[58] Field of Search ........................... 514/620, 634, 514/19; 564/164, 237, 153, 157, 159, 225; 554/35, 36, 51, 53; 530/300

[56] References Cited

U.S. PATENT DOCUMENTS

| | | | |
|---|---|---|---|
| 4,202,873 | 5/1980 | Batz et al. | 424/1 |
| 4,602,041 | 7/1986 | Newsome et al. | 514/634 |
| 4,647,693 | 3/1987 | Kondo et al. | 562/439 |
| 4,732,916 | 3/1988 | Satoh et al. | 514/620 |
| 4,873,253 | 10/1989 | Okamato et al. | 564/157 |
| 4,954,512 | 9/1990 | Oguro et al. | 514/352 |
| 4,990,536 | 2/1991 | Sakasai et al. | 514/563 |
| 5,037,808 | 8/1991 | Tjoeng et al. | 514/20 |
| 5,145,872 | 9/1992 | Chiarino et al. | 514/620 |

FOREIGN PATENT DOCUMENTS

| | | | |
|---|---|---|---|
| 0394684A1 | 10/1990 | European Pat. Off. | |
| 0432432 | 6/1991 | European Pat. Off. | 564/164 |
| 2015651 | 10/1970 | Germany. | |
| 7136605 | 10/1971 | Japan. | |

OTHER PUBLICATIONS

Abstract of Japanese patent A7136605.
Abstract of German patent DE2015691.
PCT Search Report, International Application No. PCT/US94/00335, mailed May 23, 1994.
Reynolds et al., The Journal of Pharmacology and Experimental Therapeutics, vol. 259, No. 2, pp. 626–632 (1991).

*Primary Examiner*—Shailendra Kumar
*Attorney, Agent, or Firm*—Finnegan, Henderson, Farabow, Garrett & Dunner, L.L.P.

[57] ABSTRACT

Compounds which have one of the following structural formulae:

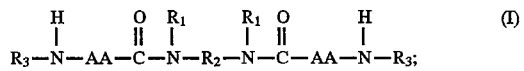

or

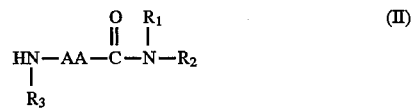

AA is an amino acid residue or an amino acid chain of two or more amino acid residues, excluding the N-terminal and the C-terminal from said amino acid residue or amino acid chain of two or more amino acid residues;

$R_1$ is hydrogen or an alkyl group having from 1 to 8 carbon atoms;

$R_2$ is selected from the group consisting of
  (i) a substituted or unsubstituted hydrocarbon having from 1 to 20 carbon atoms, and

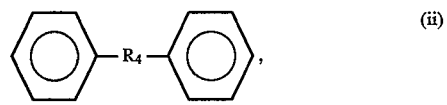

$R_4$ is an aliphatic hydrocarbon having 1 to 4 carbon atoms. $R_4$ may be substituted or unsubstituted.

$R_3$ is selected from the group consisting of
  (i) hydrogen;

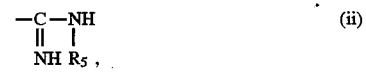

wherein $R_5$ is hydrogen or a nitro group; and

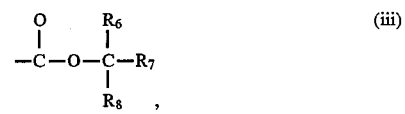

wherein each of $R_6$, $R_7$, and $R_8$ is hydrogen or methyl. The above compounds are useful as pharmaceuticals for inhibiting the growth of target cells, viruses, or virally-infected cells.

25 Claims, No Drawings

AMINO ACIDS AND PEPTIDES HAVING MODIFIED C-TERMINALS AND MODIFIED N-TERMINALS

This application is a continuation-in-part of U.S. Ser. No. 199,553, filed Feb. 22, 1994, now abandoned which is a C-I-P of U.S. Ser. No. 004,313, filed Jan. 14, 1993, now abandoned.

BACKGROUND OF THE INVENTION

This invention relates to biologically active amino acids and peptides. More particularly, this invention relates to biologically active amino acids and peptides having modified C-terminals and modified N-terminals.

Certain peptides, proteins, and dipeptides having C-terminal or N-terminal substitutions have been disclosed previously. Molinero, et al., *Peptides*, (Giralt, et al., eds., pgs. 436–437 (1990)), disclose dipeptides substituted at the N-terminal with a lauroyl group. The dipeptides have surfactant activity, as well as antimicrobial activity. Antimicrobial activity was tested against *Bacillus pumilus, Micrococcus lateus, Corynebacterium agropyri, Micrococcus lateus, Staphylococcus epidermidis, Micrococcus aurantaleus, Streptococcus faecalis*, and *Candida albicans*. Copending U.S. patent application Ser. No. 713,716, filed Jun. 12, 1991, discloses amphiphilic ion channel-forming peptides or proteins which have C-terminal substitutions. The C-terminal substitutions may be C-terminal esters, C-terminal hydrazides, C-terminal hydroxylamines, or C-terminal amides.

In accordance with an aspect of the present invention, there is provided a compound having the following structural formula:

$$\begin{array}{c} H \quad O \quad R_1 \quad\quad R_1 \quad O \quad H \\ | \quad \| \quad | \quad\quad | \quad \| \quad | \\ R_3-N-AA-C-N-R_2-N-C-AA-N-R_3 \end{array} \quad (I)$$

AA is an amino acid or a chain of two or more amino acids, excluding the N-terminus and C-terminus from the amino acid or chain of two or more amino acids.

$R_1$ is hydrogen or an alkyl group having 1 to 8 carbon atoms.

$R_2$ is selected from the group consisting of (i) a substituted or unsubstituted aliphatic (i.e., alkyl, alkenyl, or alkynl) hydrocarbon having 1 to 20 carbon atoms, and

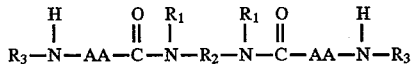 (ii)

$R_4$ is an aliphatic hydrocarbon having 1 to 4 carbon atoms. $R_4$ may be substituted or unsubstituted.

$R_3$ is selected from the group consisting of (i) hydrogen;

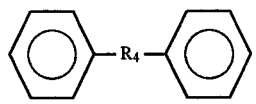 (ii)

wherein $R_5$ is hydrogen or a nitro group; and

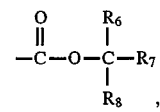 (iii)

wherein each of $R_6$, $R_7$, and $R_8$ is hydrogen or methyl.

In one embodiment, $R_1$ is hydrogen. In another embodiment, $R_1$ is an alkyl group having from 1 to 8 carbon atoms.

In another embodiment, $R_2$ is an alkyl group and preferably an alkyl group having from 7 to 16 carbon atoms.

In yet another embodiment,

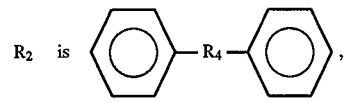

wherein $R_4$ is an aliphatic hydrocarbon having from 1 to 4 carbon atoms. Preferably, $R_4$ is an alkenyl group, more preferably an alkenyl group having from 2 to 4 carbon atoms, and most preferably $R_4$ is an alkenyl group having 2 carbon atoms.

In one embodiment, $R_3$ is hydrogen. In another embodiment, $R_3$ is:

In one embodiment, $R_3$ is hydrogen, while in another embodiment, $R_5$ is a nitro group.

In yet another embodiment, $R_5$ is

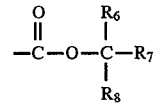

In one embodiment, each of $R_6$, $R_7$, and $R_8$ is hydrogen. In another embodiment, each of $R_6$, $R_7$, and $R_8$ is methyl.

The amino acid residues which may be contained in the compound can be amino acid residues known to those skilled in the art. Such residues include, but are not limited to, hydrophobic amino acid residues, basic hydrophilic amino acid residues, and neutral hydrophilic amino acid residues.

The hydrophobic amino acids are Ala, Cys, Gly, Ile, Leu, Met, Phe, Pro, Trp, Tyr, Val, cyclohexylalanine (Cha), norleucine (Nle), norvaline (Nva), and aminobutyric acid.

The basic hydrophilic amino acids are Lys, Arg, His, ornithine (Orn), p-aminophenylalanine, and 2,4-diaminobutyric acid (Dbu), and homoarginine (Har).

The neutral hydrophilic amino acids are Ash, Gln, Ser, Thr, and homoserine (Hae).

Within the scope of the present invention, the amino acid residue may contain substituents such as, for example, halogens, amino groups, amidino groups, or

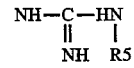

groups (wherein $R_5$ is as hereinabove described), at positions other than the carboxyl or amino terminus. For example, when a phenylalanine residue is employed, the phenylalanine residue may be substituted at one or more positions of the phenyl group with one or more of the substituents hereinabove described. As an illustrative example, the phenyl group may be substituted at the para-position with a halogen atom (such as fluorine, for example) or an amino group.

In another embodiment, AA is an amino acid or a chain of at least two and no greater than 20 amino acids, wherein the C-terminal and the N-terminal of the amino acid or chain of amino acids is excluded.

In one embodiment, one or more of the amino acid residues is a D-amino acid residue. Compounds in which one or more of the amino acid residues is a D-amino acid residue have increased resistance to proteolytic enzymes found in the gut, and thus may be administered orally.

Representative examples of such compounds of the present invention include, but are not limited to, the following:

1. [1-nitroamidino phenylalanyl-12-nitroamidino phenylalanyl]1,12 diaminododecane.

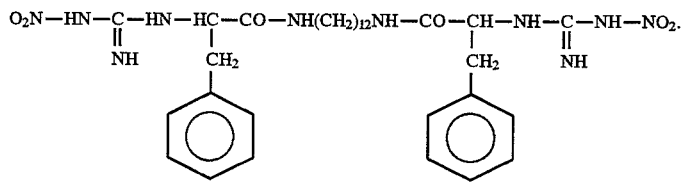

2. [1-nitroamidino phenylalanyl-12-amidino-phenylalanyl]1,12-diaminododecane.

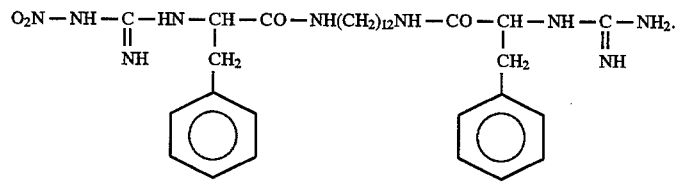

3. 1,12-[bis-N-α-amidino-phenylalanyl] diaminododecane.

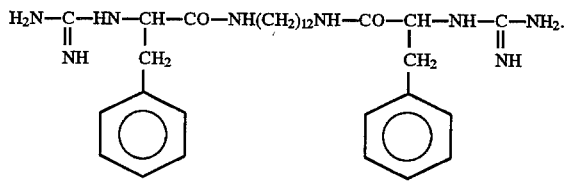

4. 1,12-[bis-N-α-amidino-tyrosyl)diaminododecane.

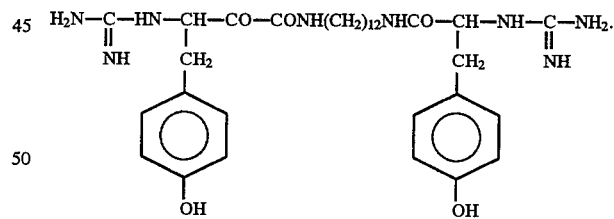

5. [1-nitroamidino-seryl-12 amidino-seryl]-1, 12-diaminododecane.

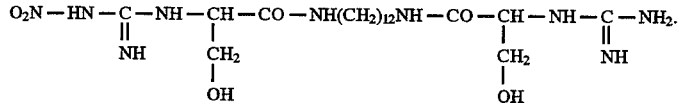

6. 1,7-[bis-N-α-amidino-phenylalanyl]diaminoheptane.
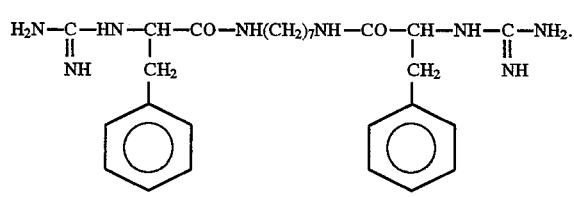
7. 1,7-[bis-N-α-amidino-seryl]diaminoheptane.
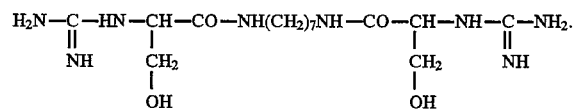
8. 1,12-[di-arginyl]diaminododecane.
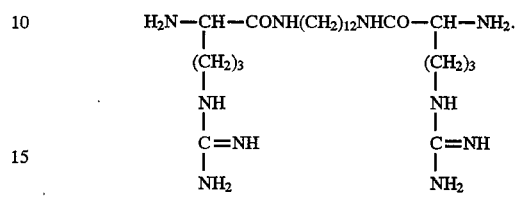
9. 1,12-[di-arginyl-phenylalanyl]diaminododecane.
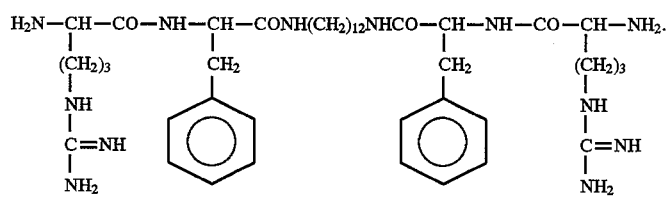
10. 1,12-[di-N-α-amidino-arginyl-phenylalanyl]diaminododecane.
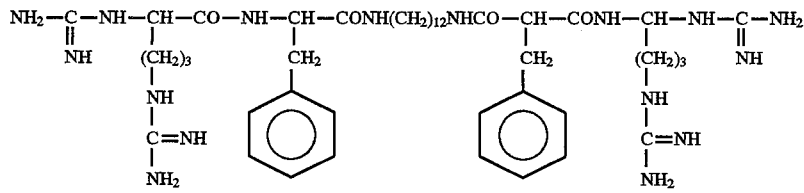
11. 1,12-[bis-N-α-amidino-p-fluoro-phenylalanyl]diaminododecane.
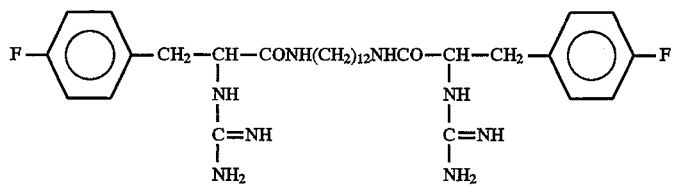
12. 1,12-[di-B-alanyl-arginyl-phenylalanyl)diaminododecane.
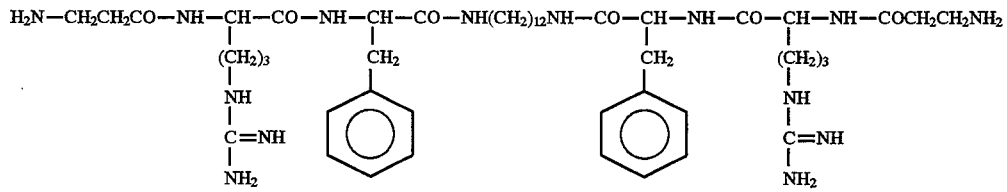

13. 1,12-[di-(N-α-amidino-seryl)]diaminododecane.
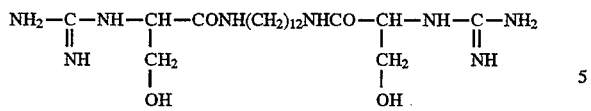
14. 1,12-[di-amidino-β-alanyl-arginyl-phenylalanyl)]diaminododecane.
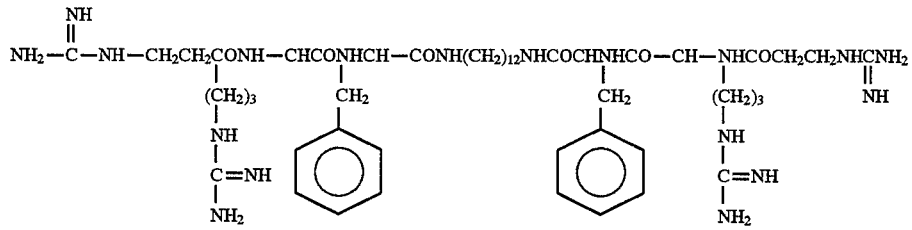
15. 1-12,-[di-[Boc-γ-aminobutyryl-arginyl-phenylalanyl)]diaminododecane.
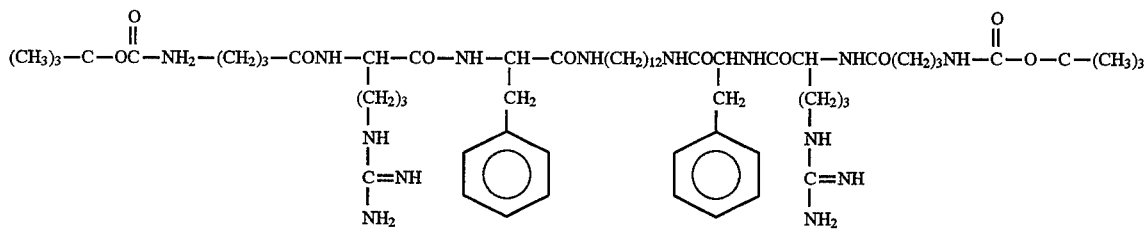
16. 1,12-[di-(Boc-alanyl-arginyl-phenylalanyl)]diaminododecane.
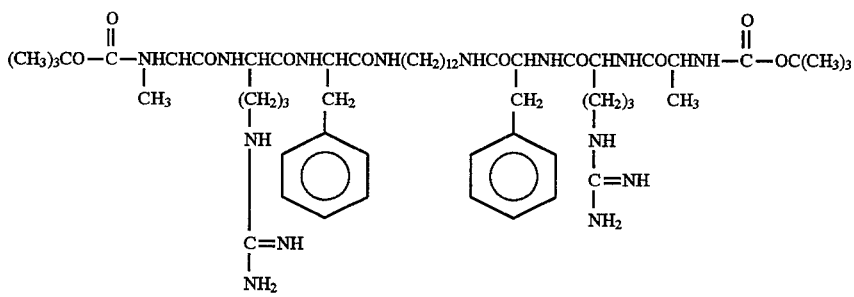
17. 1,12-[di(γ-aminobutyryl-arginyl-phenylalanyl)]diaminododecane.
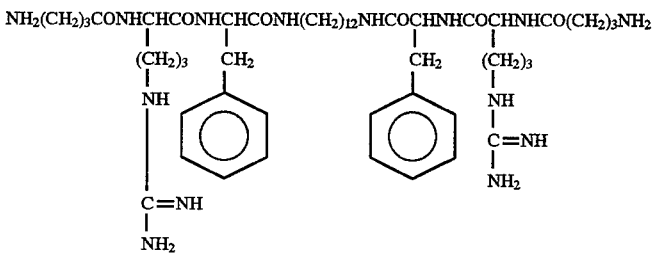

18. 1,12-[di(alanyl-arginyl-phenylalanyl)]diaminododecane.
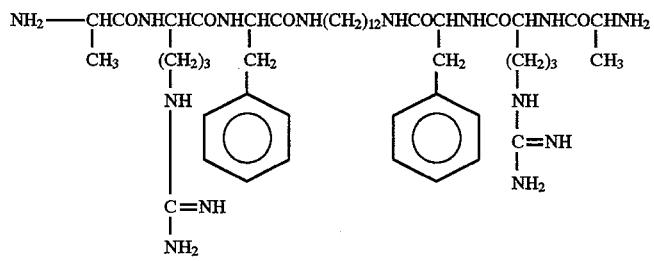
19. 1,12-[(di-(p-F-phenylalanyl)]diaminododecane.
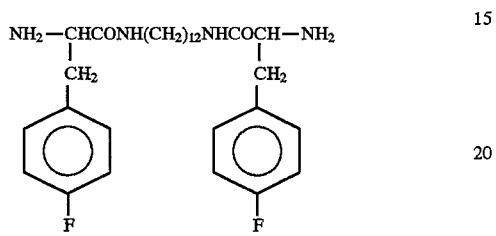
20. 1,12-[di-(arginyl-arginyl-phenylalanyl)]diaminododecane.
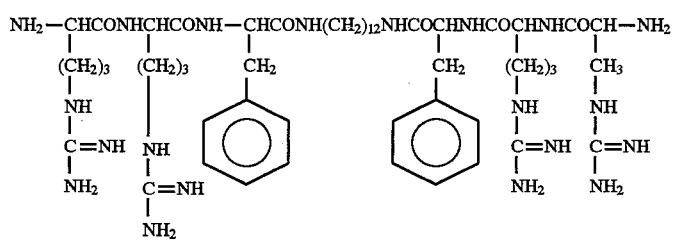
21. 1,12-[di-(glutamyl-arginyl-phenylalanyl)]diaminododecane.
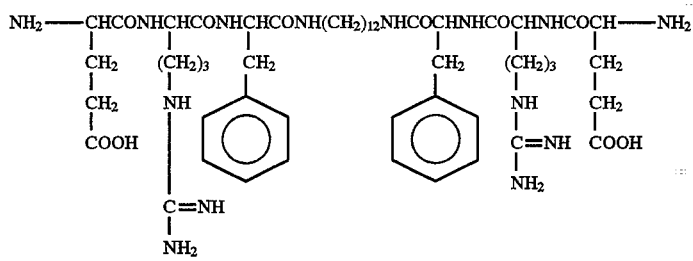
22. 1,12-[di-phenyalanyl-arginyl)]diaminododecane.
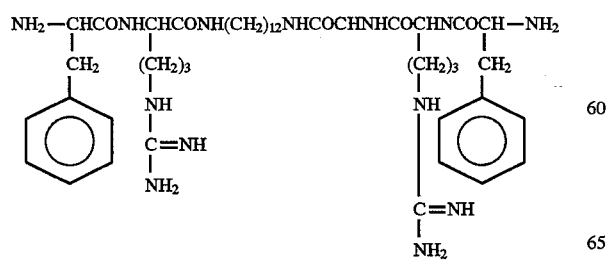

23. 1,2-[di-(arginyl-phenylalanyl-threonyl-threonyl)]diaminoethane.

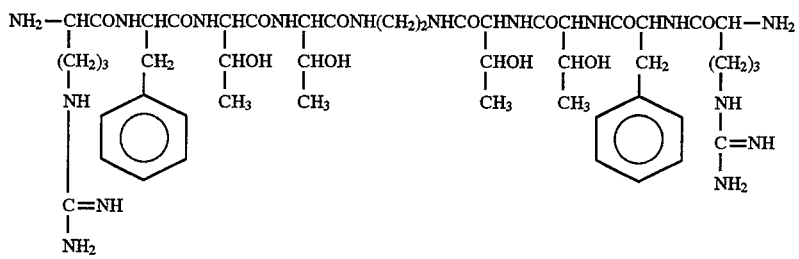

24. 4-(N-α-amidino-phenylalanyl)-4'-phenylalanyl-diaminostilbene.

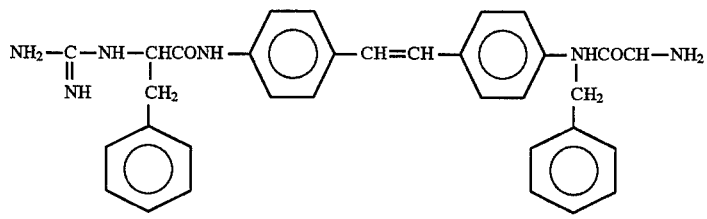

25. 4,4'-[di-(arginyl-phenylalanyl)]diaminostilbene.

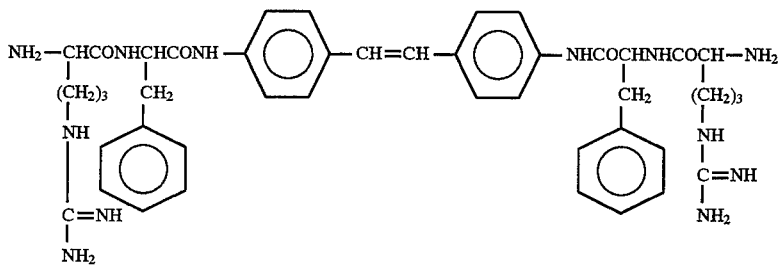

The above compounds are sometimes hereinafter referred to as Compounds 1 through 25, respectively.

In accordance with another aspect of the present invention, there is provided a compound having the following structural formula:

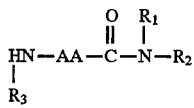

AA is an amino acid or a chain or two or more amino acids, excluding the N-terminus and C-terminus from said amino acid or chain of two or more amino acids.

$R_1$ is hydrogen or an alkyl group having from 1 to 8 carbon atoms.

$R_2$ is selected from the group consisting of
(i) a substituted or unsubstituted an aliphatic hydrocarbon having from 1 to 20 carbon atoms, and

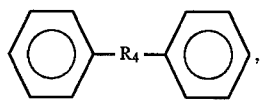

wherein $R_4$ is an aliphatic hydrocarbon having 1 to 4 carbon atoms. $R_4$ may be substituted or unsubstituted.

$R_3$ is selected from the group consisting of (i) hydrogen;

wherein $R_5$ is hydrogen or a nitro group; and

wherein each of $R_6$, $R_7$, and $R_8$ is hydrogen or methyl.

In one embodiment, $R_1$ is hydrogen. In another embodiment, $R_1$ is an alkyl group having from 1 to 8 carbon atoms.

In a preferred embodiment, $R_2$ is an alkyl group, and preferably an alkyl group having from 7 to 16 carbon atoms.

In another embodiment,

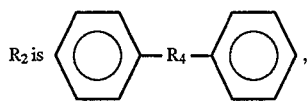

wherein $R_4$ is an aliphatic hydrocarbon having from 1 to 4 carbon atoms. Preferably, $R_4$ is an alkenyl group, more preferably an alkenyl group having from 2 to 4 carbon atoms, and most preferably $R_4$ is an alkenyl group having 2 carbon atoms.

In one embodiment, $R_3$ is hydrogen. In another embodiment, $R_3$ is:

wherein $R_5$ is hydrogen or a nitro group.

In one embodiment, $R_5$ is hydrogen, whereas in another embodiment, $R_5$ is a nitro group.

In another embodiment, $R_3$ is:

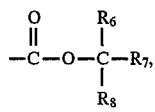

wherein each of $R_6$, $R_7$, and $R_8$ is hydrogen or methyl.

In one embodiment, each of $R_6$, $R_7$, and $R_8$ is hydrogen. In another embodiment, each of $R_6$, $R_7$, and $R_8$ is methyl.

In another embodiment, AA is an amino acid or a chain of at least two and no greater than 20 amino acids, excluding the C-terminal and the N-terminal of the amino acid or chain of at least two and no greater than 20 amino acids.

The amino acid(s) which are part of the compound may be those hereinabove described. The amino acid residue(s) may be substituted at positions other than the carboxyl terminus or the amino terminus with substituent groups such as those hereinabove described. In one embodiment, the amino acid (s) is a hydrophobic amino acid residue, and preferably a phenylalanine residue. When the amino acid residue is a phenylalanine residue, such residue may, in one embodiment, be further modified such that the compound has the following structural formula:

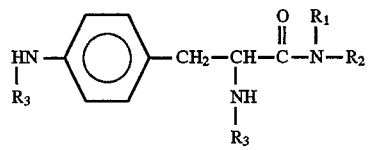

wherein $R_1$, $R_2$, and $R_3$ are as hereinabove described. In one embodiment, $R_3$ is hydrogen, and in another embodiment, $R_3$ is:

wherein $R_5$ is as hereinabove described. In one embodiment, $R_5$ is hydrogen, whereas in another embodiment, $R_5$ is a nitro group.

Each of the amino acid residue(s) which is not a glycine residue, may be a D-amino acid residue.

Representative examples of compounds having the structural formula hereinabove described include the following:

26. phenylalanyl heptylamide.

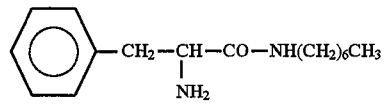

27. N-α-amidino phenylalanyl heptylamide.

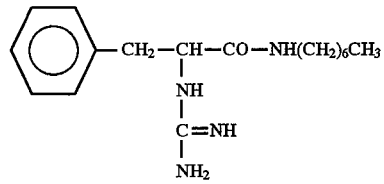

28. p-amino-phenylalanyl heptylamide.

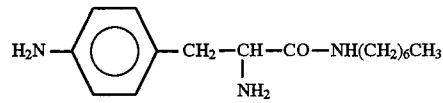

29. p-guanyl-N-α-amidino-phenylalanyl heptylamide.

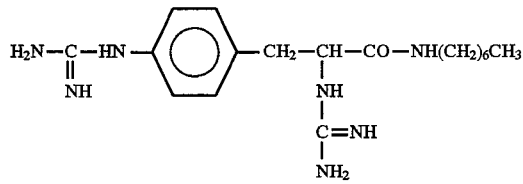

30. p-amino-N-α-amidino-phenylalanyl heptylamide.

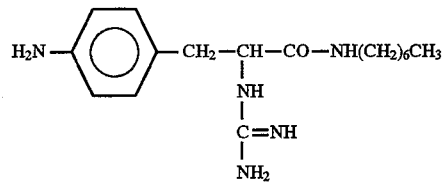

31. N-α-amidino-phenylalanyl dodecylamide.

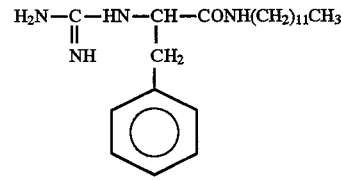

32. N-α-amidino-phenylalanyl dioctylamide.

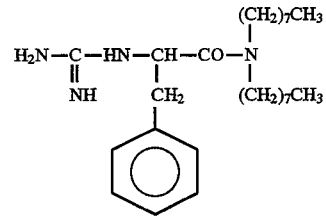

33. N-α-amidino phenylalanyl tetradecylamide.

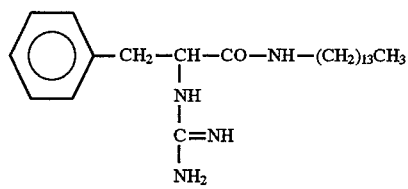

34. N-α-amidino phenylalanyl hexadecylamide.

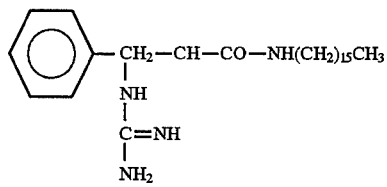

35. arginyl-phenylalanyl dioctylamide.

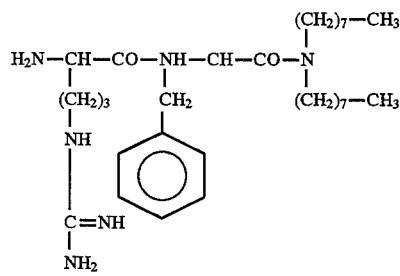

Such compounds are sometimes hereinafter referred to as Compounds 26 through 35, respectively.

In accordance with another aspect of the present invention, there is provided a process for inhibiting the growth of a target cell, virus, or virally-infected cell in a host. The process comprises administering to a host a compound having the following structural formula:

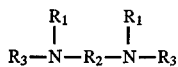

$R_1$, $R_2$ and $R_3$ are as hereinabove described. In one embodiment, $R_1$ is hydrogen. In another embodiment, $R_3$ is:

wherein $R_5$ is hydrogen or a nitro group. In one embodiment, $R_5$ is hydrogen, whereas in another embodiment, $R_5$ is a nitro group.

A representative example of such a compound which may be administered in accordance with the present invention is 1,12 [bisguanyl]diaminododecane, which has the following structure:

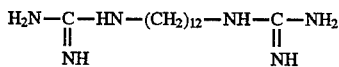

This compound is sometimes hereinafter referred to as Compound 36.

In general, such compounds may be prepared from a diaminoalkane, which may be reacted with 1-methyl-3-nitro-1-nitrosoguanidine, and the nitro-guanylated product is the hydrogenated and purified by preparative HPLC to obtain the desired compound.

The compounds of the present invention may be administered to a host; for example a human or non-human animal, in an amount effective to inhibit growth of a target cell or virus. Thus, for example, the compounds may be used as antimicrobial agents, anti-vital agents, anti-bacterial agents, anti-tumor agents, anti-parasitic agents, spermicides, as well as-exhibiting other bioactive functions.

The term "antimicrobial" as used herein means that the compounds of the present invention inhibit, prevent, or destroy the growth or proliferation of microbes such as bacteria, fungi, viruses, or the like.

The term "anti-bacterial" as used herein means that the compounds employed in the present invention produce effects adverse to the normal biological functions of bacteria, including death or destruction and prevention of the growth or proliferation of the bacteria when contacted with the compounds.

The term "antibiotic" as used herein means that the compounds employed in the present invention produce effects adverse to the normal biological functions of the non-host cell, tissue or organism, including death or destruction and prevention of the growth or proliferation of the non-host cell, tissue, or organism when contacted with the compounds.

The term "spermicidal" as used herein means that the compounds employed in the present invention, inhibit, prevent, or destroy the motility of sperm.

The term "antiviral" as used herein means that the compounds employed in the present invention inhibit, prevent, or destroy the growth or proliferation of viruses, or of virally-infected cells.

The term "anti-tumor" as used herein means that the compounds inhibit the growth of or destroy tumors, including cancerous tumors.

The term "anti-parasitic" as used herein means that the compounds employed in the present invention inhibit, prevent, or destroy the growth or proliferation of parasites.

The compounds of the present invention have a broad range of potent antibiotic activity against a plurality of microorganisms including gram-positive and gram-negative bacteria, fungi, protozoa, and the like, as well as parasites. The compounds of the present invention allow a method for treating or controlling microbial infection caused by organisms which are sensitive to the compounds. Such treatment may comprise administering to a host organism or tissue susceptible to or affiliated with a microbial infection an antimicrobial amount of at least one of the compounds.

Because of the antibiotic, antimicrobial, antiviral, and antibacterial properties of the compounds, they may also be used as preservatives or sterilants or disinfectants of materials susceptible to microbial or viral contamination.

The compounds may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The compositions containing the compounds of the present invention may also be used in combination with adjuvants, protease inhibitors, or compatible drugs where such a combination is seen to be desirable or advantageous in controlling infection caused by harmful microorganisms including protozoa, viruses, and the like, as well as by parasites.

The compounds of the present invention may be administered to a host; in particular a human or non-human animal, in an effective antibiotic and/or anti-tumor and/or anti-viral and/or antimicrobial and/or antibacterial and/or antiparasitic and/or an antispermicidal amount.

Depending on the use, a composition in accordance with the invention will contain an effective anti-microbial amount and/or an effective-antispermicidal amount and/or an effective anti-viral amount and/or an effective anti-tumor amount and/or an effective anti-parasitic and/or an effective antibiotic amount of one or more of the hereinabove described compounds which have such activity. The compounds may be administered by direct application of the compounds to the target cell or virus or virally-infected cell, or indirectly applied through systemic administration.

The compounds of the present invention may also be employed in promoting or stimulating healing of a wound in a host.

The term "wound healing" as used herein includes various aspects of the wound healing process.

These aspects include, but are not limited to, increased contraction of the wound, increased deposition of connective tissue, as evidenced by, for example, increased deposition of collagen in the wound, and increased tensile strength of the wound, i.e., the compounds increase wound breaking strength. The compounds of the present invention may also be employed so as to reverse the inhibition of wound healing caused by conditions which depress or compromise the immune system.

The compounds of the present invention may be used in the treatment of external burns and to treat and/or prevent skin and burn infections. In particular, the compounds may be used to treat skin and burn infections caused by organisms such as, but not limited to, *P. aeruginosa* and *S. aureus*.

The compounds are also useful in the prevention or treatment of eye infections. Such infections may be caused by bacteria such as, but not limited to, *P. aeruginosa*, *S. aureus*, and *N. gonorrhoea*, by fungi such as but not limited to *C. albicans* and *A. fumigatus*, by parasites such as but not limited to *A. castellani*, or by viruses.

The compounds may also be effective in killing cysts, spores, or trophozoites of infection—causing organisms. Such organisms include, but are not limited to Acanthamoeba which forms trophozoites or cysts, *C. albicans*, which forms spores, and *A. fumigatus*, which forms spores as well.

The compounds may also be administered to plants in an effective antimicrobial or antiviral or antiparasitic amount to prevent or treat microbial or viral or parasitic contamination thereof.

The compounds, when used in topical compositions, are generally present in an amount of at least 0.1%, by weight. In most cases, it is not necessary to employ the compound in an amount greater than 2.0%, by weight.

In employing such compositions systemically (intramuscular, intravenous, intraperitoneal), the compound is present in an amount to achieve a serum level of the compound of at least about 5 ug/ml. In general, the serum level of the compound need not exceed 500 ug/ml. A preferred serum level is about 100 ug/ml. Such serum levels may be achieved by incorporating the compound in a composition to be administered systemically at a dose of from 1 to about 100 mg/kg. In general, the compound need not be administered at a dose exceeding 10 mg/kg.

The compounds of the present invention, having modified C-terminals and modified N-terminals, may be prepared by any acceptable methods for modifying the C-terminal and the N-terminal of amino acids or peptides to provide the compounds hereinabove described. For example, an amino acid or peptide may be reacted with an alkyl amine in the presence of 1,3-dicyclohexylcarbodiimide (DCC) to form an amino acid or peptide having an alkyl amide at the C-terminal. The C-terminal modified amino acid or peptide may then be reacted with a guanyl group to form an amino acid or peptide having an alkyl amide at the C-terminal and a guanyl group at the N-terminal. It is to be understood, however, that the scope of the present invention is not to be limited to any specific moieties at the C-terminal or N-terminal, or to any specific reaction scheme for preparing the compounds.

The amino acids or peptides (including 2 or more amino acids), prior to the modification thereof, may be obtained in substantially pure form. When a peptide is desired to be modified in accordance with the present invention, the unmodified peptide may be synthesized on an automatic peptide synthesizer. *Journal of the American Chemical Society*, Vol. 85, pgs. 2149–54 (1963). It is also possible to produce unmodified peptides by genetic engineering techniques.

Thus, within the scope of the present invention there may be provided DNA which encodes the peptides prior to the modification thereof. Such DNA may be expressed by means known to those skilled in the art.

In accordance with another embodiment, the compounds may be employed in combination with an ion having pharmacological properties for the purposes hereinabove described.

An ion having pharmacological properties is one which when introduced into a target cell, virus, or virally infected cell, inhibits and/or prevents and/or destroys the growth of the target cell, virus, or virally-infected cell.

Such an ion having pharmacological properties is one which in the absence of an ion channel-forming peptide is unable to cross a natural or synthetic lipid membrane; in particular a cell membrane, in sufficient amounts to affect a cell or virus adversely.

The compound and ion having pharmacological properties may be administered as a single composition or in separate compositions, and the single or separate compositions may include additional materials, actives and/or inactives, in addition to the compound and ion having pharmacological properties. As representative examples of ions having pharmacological properties which may be employed, there may be mentioned fluoride, peroxide, bicarbonate, silver, zinc, mercury, arsenic, copper, platinum, antimony, gold, thallium, nickel, selenium, bismuth, and cadmium ions.

The compound and the ion having pharmacological properties, whether administered or prepared in a single composition or in separate compositions, are employed in amounts effective to inhibit and/or prevent and/or destroy the growth of the target cell. In effect, the ion potentiates the action of the compound, i.e., the amount of ion is effective to reduce the minimum effective concentration of the compound for inhibiting growth of a target cell, virus, or virally-infected cell.

The ion having pharmacological properties, when used topically, is generally employed in a concentration of from 0.05% to 2.0%. When used systemically, the ion is generally employed in an amount of from 1 to 10 mg. per kg. of host weight. Dosages of the compound may be within the ranges hereinabove described.

It is also to be understood that the compound and ion having pharmacological properties, may be delivered or administered in different forms; for example, the ion may be administered orally, while the compound may be administered by IV or IP.

As representative examples of administering the compound and ion for topical or local administration, the compound could be administered in an amount of up to about 1% weight to weight and the ion delivered in an amount of about 50 mM (about 0.1%). Alternatively, the ion, in the form of a salt such as sodium fluoride, could be administered orally in conjunction with systemic administration of the compound. For example, the compound may be administered IV or IP to achieve a serum dose of 100 micrograms per milliliter (10 milligrams per kilogram) in conjunction with an oral dose of ion, in particular, sodium fluoride, of 10 meq per kilogram.

In accordance with another embodiment, the compounds of the present invention may be administered to a host in combination with an antibiotic selected from the class consisting of bacitracins, gramicidin, polymyxin, vancomycin, teichoplanin, aminoglycosides, pseudomonic acids, cephalosporins, penem antibiotics, hydrophobic antibiotics, penicillins, monobactams, or derivatives or analogues thereof.

The bacitracins, gramicidin, polymyxin, vancomycin, teichoplanin, and derivatives and analogues thereof, are a group of polypeptide antibiotics. A preferred bacitracin is bacitracin A.

Aminoglycoside antibiotics include tobramycin, kanamycin, amikacin, the gentamicins (e.g., gentamicin $C_1$, gentamicin $C_2$, gentamicin $C_{1a}$), netilmicin, and derivatives and analogues thereof. The preferred aminoglycosides are tobramycin and the gentamicins. The aminoglycosides, and the bacitracins hereinabove described, tend to be hydrophilic and water-soluble.

Penicillins which may be employed include, but are not limited to benzyl penicillin, ampicillin, methicillin (dimethoxyphenyl penicillin), ticaricillin, penicillin V (phenoxymethyl penicillin), oxacillin, cloxacillin, dicloxacillin, flucloxacillin, amoxicillin, and amidinocillin. Preferred penicillins which may be employed are benzyl penicillin and ampicillin. A preferred monobactam which may be employed is aztreonam.

As representative examples of hydrophobic antibiotics which may be used in the present invention, there may be mentioned macrolides such as erythromycin, roxythromycin, clarithromycin, etc.; 9-N-alkyl derivatives of erythromycin; midecamycin acetate; azithromycin; flurithromycin; rifabutin; rokitamycin; a 6-0-methyl erythromycin A known as TE-031 (Taisho); rifapentine; benzypiperazinyl rifamycins such as CGP-7040, CGP-5909, CGP-279353 (Ciba-Geigy); an erythromycin A derivative with a cyclic carbamate fused to the $C_{11}/C_{12}$ position of a macrolide ring known as A-62514 (Abbott); AC-7230 (Toyo Jozo); benzoxazinorifamycin; difficidin; dirithromycin; a 3-N-piperdinomethylzaino methyl rifamycin SV known as FCE-22250 (Farmitalia); M-119-a (Kirin Brewery); a 6-0-methyl-1-4"-0-carbamoyl erythromycin known as A-63075 (Abbott); 3-formylrifamycin SV-hydrazones with diazabicycloalkyl side chains such as CGP-27557 and CGP-2986 (Ciba-Geigy); and 16-membered macrolides having a 3-0-alpha-L-cladinosyl moiety, such as 3-0-alpha-L-cladinosyldeepoxy rosaramicin; tylosins and acyl demycinosyl tylosins.

In addition to the macrolides hereinabove described, rifamycin, carbenicillin, and nafcillin may be employed as well.

Other antibiotics which may be used (whether or not hydrophobic) are antibiotics which are 50-S ribosome inhibitors such as lincomycin; clindamycin; and chloramphenicol; etc.; antibiotics which have a large lipid like lactone ring, such as mystatin; pimaricin, etc.

The compound and antibiotic may be administered by direct administration to a target cell or by systemic or topical administration to a host which includes the target cell, in order to prevent, destroy or inhibit the growth of a target cell. Target cells whose growth may be prevented, inhibited, or destroyed by the administration of the compounds and antibiotic include Gram-positive and Gram-negative bacteria as well as fungal cells.

The antibiotic, such as those hereinabove described, or derivatives or analogues thereof, when used topically, is generally employed in a concentration of about 0.1% to about 10%. When used systemically, the antibiotic or derivative or analogue thereof is generally employed in an amount of from 1.25 mg. to about 45 mg. per kg. of host weight per day. Dosages of the compound may be those as hereinabove described.

As representative examples of administering the compound and antibiotic for topical or local administration, the compound could be administered in an amount of from about 0.1% to about 10% weight to weight, and the antibiotic is delivered in an amount of from about 0.1% to about 10% weight to weight.

In accordance with another embodiment, the compounds of the present invention may be administered in combination with an antiparasitic agent or an antifungal agent.

Antiparasitic agents which may be employed include, but are not limited to, anti-protozoan agents. Examples of specific antiparasitic agents which may be employed include, but are not limited to, pentamidine isethionate, and propamidine isethionate (Brolene).

Anti-fungal agents which may be employed include, but are not limited to, ketoconazole. It is also to be understood that certain anti-parasitic agents, may also have anti-fungal activity, and that certain anti-fungal agents may have anti-parasitic activity.

In accordance with another embodiment, the compounds of the present invention may be administered in combination with an antibiotic which inhibits DNA gyrase, which is an enzyme involved in the formation of bonds between individual coiling strands of replicating bacterial DNA. Thus, DNA gyrase is necessary for the normal replication of bacterial DNA, and, therefore, antibiotics which inhibit DNA gyrase inhibit the normal replication of bacterial DNA.

Examples of antibiotics which inhibit DNA gyrase include nalidixic acid, oxolinic acid, cinoxacin, and quinolone antibiotics which include ciprofloxacin, norfloxacin, ofloxacin, enoxacin, pefloxacin, lomefloxacin, fleroxacin, tosulfloxacin, temafloxacin, and rufloxacin.

In accordance with another embodiment, the compounds of the present invention may be administered for the purpose hereinabove described in combination with biologically active amphiphilic peptides, or in combination with ion channel-forming proteins.

The present invention will be further described with respect to the following examples; however, the scope of the invention is not to be limited thereby.

EXAMPLE 1

A. Procedures for the Preparation of Compounds
Procedure (i)

N-α-tert-butyloxycarbonyl (Boc) amino acid(s) was (were) placed into a DMF or $DMF/CH_2Cl_2$ (10 ml/g) solvent system, and an equivalent amount of 1-hydroxybenzotriazole (HOBt) was added and the mixture was stirred in an ice-salt temperature bath. A coupling reagent, 1-ethyl-3-dimethylaminopropyl carbodiimide/Hcl (equimolar amounts) was added and stirring continued for 20 minutes at about −15° C. To this reaction mixture, an amino component (either as an alkyl amine or a suitably protected amino acid), as a free base, was added and stirring continued overnight at room temperature. After concentrating the solvent to about half the original volume the reaction mixture was poured into a cold stirred solution of $NaHCO_3$. After stirring for about 30 minutes the precipitate was filtered, washed with water, then 5% citric acid, then water, and then dried. The homogeneity of the product was checked by thin layer chromatography (TLC) in different solvent systems.

In instances where the peptide did not precipitate out, the aqueous solution was extracted with ethyl acetate or chloroform. The organic phase was separated and washed with 5% $NaHCO_3$ solution, water, 5% citric acid, water, dried over anhyd. $Na_2SO_4$ and solvent removed under reduced pressure to obtain the desired product.

Procedure (ii)

The compound was then treated with either trifluoroacetic acid (TFA) or 50% TFA in $CHCl_3$ (10 ml/g) for 30 minutes, and concentrated at reduced pressure at about 30° C. in order to remove the Boc group. The residue was treated with ether, filtered, washed with ether, petroleum ether, and then dried.

Sometimes, a free base was generated by taking the trifluoroacetate salt obtained above into chloroform and extracting with 5% $NaHCO_3$ solution followed by water. The organic phase was dried over anhyd. $Na_2SO_4$ and solvent removed under reduced pressure to obtain the free base.

Procedure (iii)—Guanylation

The residue was then treated with 1-methyl-3-nitro-1-nitrosoguanidine at about 55° C. for several days while following the progress of the reaction by thin layer chromatography. Solvent was removed under reduced pressure, triturated with ether and decanted. The residue then was triturated with water and decanted. The nitroguanylated product was purified in some cases and checked for antibacterial activities. The crude product was placed into a mixture of $CH_3OH$:acetic acid:water (9:1:1), and hydrogenated overnight at 40 psi in the presence of 10% Pd/C catalyst (0.5–1.0 equivalent amount by weight). The catalyst was filtered and concentrated in vacuo. The residue was triturated with ether, filtered, washed with ether, and then with petroleum ether, and then dried. The purification of the compound was carried out by reverse phase HPLC (C-18 Dynamax, 300A). The homogeneity of the product was checked by thin layer chromatography and mass spectrometry.

Procedure (iv)

Alternatively, guanylation was achieved by refluxing the amino compound in ethanol with 3,5-dimethylpyrazole-1-carboxamidine.$HNO_3$ and an equivalent amount of triethylamine. The progress of the reaction was followed either by TLC or by HPLC. After removing the solvent the product was purified either by crystallization or by reverse phase HPLC.

Procedure (v) (Di-, Tri- and Tetra peptide analogs)

Following the initial coupling of the first amino acid and deblocking of the N-amino protecting group according to the procedures i and ii, the subsequent amino acids were coupled by repeating the above steps.

Procedure (vi)

Protected amino acid was treated with bis-[(2-oxo-3-oxazolidinyl)phosphinic chloride], BOP-Cl and triethylamine at ice bath temperature. Dioctylamine was added and stirred overnight in a cold room, and then at room temperature for one more day. Solvent was removed and the residue was placed in ethyl acetate and extracted with 0.5N HCl, water, 5% $NaHCO_3$ solution, water and then dried over anhydrous $Na_2SO_4$. The solvent was removed, and the product was characterized by thin layer chromatography.

Procedure (vii) (Disulfide Bond Formation)

The partially protected peptide with acetamidomethyl (Acm) groups still present on the sulfhydryl side chain of cysteines was taken into acetic acid-water (90:10) at 0.2 mmol concentration and treated with 75 equiv. of iodine in acetic acid and stirred overnight at room temperature. Acetic acid was removed under reduced pressure, the residue was taken into water and decolorized with 0.1M ascorbic acid in 0.5M citric acid solution. The product was purified by reverse phase HPLC.

Procedure (viii) (Reductive Alkylation)

To the amino compound in 1%HOAc/MeOH was added the aldehyde (e.g., Imidazole-2-aldehyde 1.5 equiv.) at ice-cold temperature. Sodium cyanoborohydride (2.5 equiv.) in 1%HOAc/MeOH was added slowly over a period of 45–60 min. After removing the solvent the product was purified by reverse phase HPLC.

Procedure (ix) (Preparation of the Esters)

The N-protected amino acid in $CH_2Cl_2$ or $CHCl_3$ was reacted with an alcohol (e.g. dodecyl alcohol) in the presence of a coupling agent, EDCI and dimethylaminopyridine in equimolar amounts. After diluting further with the same solvent, the organic phase was extracted with water, 5% $NaHCO_3$, 5% citric acid, water, dried over anhyd. $Na_2SO_4$ and solvent removed under reduced pressure to yield the product which is checked by TLC and HPLC for homogeneity.

B. Preparation of Compound 26

Compound 26 was prepared by following Procedures (i) and (ii).

C. Preparation of Compounds 28 and 29

Compound 28 was prepared by reacting N-α-Boc-p-benzyloxycarbonyl (Z) amino phenylalanine with heptylamine followed by treatment with HBr/hydroxyacetate and neutralization.

Compound 29 was prepared from Compound 15 by following Procedure (iii).

D. Preparation of Compound 30

Compound 30 was prepared by reacting N-α-Boc-p-NH (Z) phenylalanine with heptylamine after phenylalanine was subjected to Procedure (i), and then subjecting the product to Procedures (ii) and (iii).

E. Preparation of Compound 32

Compound 32 was made according to the procedures of vi, ii, and iii.

F. Preparation of Compound 35

Compound 32 was deblocked according to Procedure (ii), and coupled with BOC-arginine ($NO_2$)—OH. Hydrogenolysis followed by TFA treatment yielded Compound 35.

G. Preparation of Compound 36

1,12-diaminododecane was reacted with 1-methyl-3-nitro-1-nitrosoguanidine at about 55° C. for several days while following the progress of the reaction by thin layer chromatography. Solvent was removed under reduced pressure, triturated with ether and decanted. The residue then was triturated with water and decanted. The nitroguanylated product was purified in some cases and checked for antibacterial activities. The crude product was placed into a mixture of $CH_3OH$:acetic acid:water (9:1:1), and hydrogenated overnight at 40 psi in the presence of 10% Pd/C catalyst (0.5–1.0 equivalent amount by weight). The catalyst was filtered and concentrated in vacuo. The residue was triturated with ether, filtered, washed with ether, and then with petroleum ether, and then dried. The purification of the compound was carried out by preparative HPLC to obtain the desired compound.

H. Preparation of Compounds 37–91

Compounds 37 and 38 were prepared following the procedures i, ii and iv;

Compound 39 was prepared following the procedures i, ii, v and iv;

Compounds 40 and 41 were prepared following the procedures i, ii and v;

Compounds 42–46, 48, 51, 52 and 54–63 were prepared following the procedures i, ii, v and ii;

Compound 47 was prepared following the procedures i, ii and v;

Compound 49 was prepared following the procedures i and ii;

Compounds 50 and 53 were prepared following the procedures i, ii, v, ii and vii;

Compound 64 was prepared following the procedures vi, ii, v and iii;

Compound 65 was prepared following the procedures vi, ii and v;

Compounds 66–70, 74, 78, 83 and 88 were prepared following the procedures vi, ii and v;

Compounds 71, 72, 75 and 79 were prepared following the procedures vi, ii and iii;

Compounds 76, 77 and 86 were prepared following the procedures i, ii and iii;

Compound 80 was prepared following the procedures vi, ii and viii;

Compounds 82, 84, 85 and 87 were prepared following the procedures i, ii and iv;

Compounds 89 and 90 were prepared following the procedures vi, ii and v; and

Compound 91 was prepared following the procedures vi, ii, v and iii.

EXAMPLE 2

Antimicrobial Assay

The procedure for the antimicrobial assay is based upon the guidelines of the National Committee for Clinical Laboratory Standards, Document M7-T2, Volume 8, No. 8, 1988.

Stock solutions of Compounds 3, 4, 6, and 8 through 12, 26, 27, 29, and 31 through 36, as well as Compounds 3-D, 9-D, 12-D, wherein each of the amino acid residues of Compounds 3, 9 and 12 is D-amino acid residue, are prepared as hereinabove described in Example 1, at a concentration of 512 µg/ml in sterile deionized distilled water and stored at −70° C.

The stock modified solutions of Compounds 1 through 12, 26 through 36, and 3-D, 9-D, and 12-D are diluted in serial dilutions (1:2) down the wells of a microtiter plate so that the final concentrations of the compounds in the wells are 0.25, 0.50, 1, 2, 4, 8, 16, 32, 64, 128, and 256 µg/ml. $1-5\times10^5$ CFUs/ml of either *S. aureus* ATCC 25923, *E. coli* ATCC 25922, *P. aeruginosa* ATCC 27853, or *C. albicans* were added to the wells in full strength Mueller Hinton broth (BBL 11443) from a mid-log culture. The inoculum is standardized spectrophotometrically at 600 nm and is verified by colony counts. The plates are incubated for 16–20 hours at 37° C., and the minimal inhibitory concentrations (MIC) for the compounds are determined. Minimal inhibitory concentration is defined as the lowest concentration of amino acid or peptide which produces a clear well in the microtiter plate.

The MIC values for each of Compounds 3, 4, 6, and 8 through 12, 26, 27, 29, and 31 through 36, and 3-D, 9-D and 12-D, against *S. aureus, P. aeruginosa, E. coli,* and *C. albicans* are given in Table I below.

TABLE I

| Compound | MIC (µg/ml) | | | |
|---|---|---|---|---|
| | S. aureus | P aeruginosa | E. coli | C. albicans |
| 3 | 1 | 8 | 4 | 4 |
| 3-D | 0.25 | 16 | 2 | 2 |
| 4 | 2 | 128 | 128 | >256 |
| 6 | 64 | >256 | >256 | 256 |
| 8 | 128 | >256 | >256 | >256 |
| 9 | 4 | 64 | 16 | 32 |
| 9-D | 4 | 16 | 8 | 16 |
| 10 | 1 | 4 | 2 | 16 |
| 11 | 2 | 8 | 4 | 16 |
| 12 | 2 | 16 | 16 | 32 |
| 12-D | 4 | 64 | 16,32 | 64 |
| 26 | 256 | >256 | 128 | 128 |
| 27 | 8 | 128 | 128 | 64 |
| 29 | 64 | >256 | >256 | 256 |
| 31 | 2 | 64 | 8 | 4 |
| 32 | 1,2 | 128 | 8 | 2 |
| 33 | 8 | >256 | 128 | 16 |
| 34 | 32 | >256 | >256 | 64 |
| 35 | 4,8 | 16 | 4 | 16 |
| 36 | 8 | 128 | 32 | 32 |

EXAMPLE 3

Compounds 9-D, 12-D, 15, 16, 17, and 18 were prepared as described in Example 1, and were tested for minimal inhibitory concentration against various organisms listed in Table II according to the assay procedure given in Example 2. The results are given in Table II below.

TABLE II

| Organism | MIC (µg/ml) Compound | | | | | |
|---|---|---|---|---|---|---|
| | 9-D | 12-D | 15 | 16 | 17 | 18 |
| S. aureue 29313 | 4 | 4 | 2 | 2 | 4,8 | 16,32 |
| E. coli 25922 | 8 | 16,32 | >256 | 32 | 32 | 128 |
| P. aeruainosa 27853 | 16 | 64 | >256 | >256 | 64 | 256 |
| E. faecium 26143 | 8 | 16 | N/A | N/A | 16 | N/A |
| E. faecalis 19052 | 64 | 64 | N/A | N/A | 64 | N/A |
| E. faecalis 19290 | N/A | N/A | N/A | N/A | 64 | N/A |
| E. faecalis 23296 | N/A | N/A | N/A | N/A | 32 | N/A |
| E. faecalis 29212 | N/A | N/A | N/A | N/A | 16 | N/A |
| C. difficils TTU614 | 32 | N/A | 16,32 | N/A | N/A | N/A |
| C. diffieils P324 | 4 | N/A | 2,4 | 2 | 8,16 | 16,32 |
| B. fragilis 25285 | 16 | N/A | 16 | 2 | 16 | 64 |
| L. fermentus 23271 | 2 | N/A | 16 | 4,8 | 16,32 | 16 |
| P. gingvalis 381 | N/A | 16,32 | N/A | N/A | N/A | N/A |
| P. gingvalis FAY-19M-1 | N/A | 32 | N/A | N/A | N/A | N/A |
| P. gingvalis 9-14K-1 | N/A | 32 | N/A | N/A | N/A | N/A |
| P. gingvalis W50 | N/A | 64 | N/A | N/A | N/A | N/A |
| P. gingvalis A7A1-28 | 16 | 64 | N/A | N/A | N/A | N/A |
| C. albicans 14053 | 16 | 64 | >256 | 64 | 64 | 128 |
| C. tropicalis 13803 | 2 | 8 | N/A | N/A | N/A | N/A |
| C. tropicalis 28707 | 1 | 2 | N/A | N/A | N/A | N/A |
| C. parapsilosis 10233 | 128 | 256 | N/A | N/A | N/A | N/A |
| C. parpsilosis 22109 | 4 | 16 | N/A | N/A | N/A | N/A |
| C. kefyr 28838 | 2 | 8 | N/A | N/A | N/A | N/A |
| T. mentagrophytes 18748 | 8 | 4 | N/A | N/A | 8 | N/A |
| T. rubrum 36262 | 8 | 16 | N/A | N/A | 32 | N/A |
| M. canis 11621 | 16 | 8 | N/A | N/A | 16 | N/A |
| E. flocossum 52062 | 16 | 8 | N/A | N/A | 8 | N/A |

EXAMPLE 4

Compounds 3-D, 6, 10, 11, 12, and 14 were prepared as described in Example 1, and tested for minimal inhibitory concentration against various organisms according to the assay procedure of Example 2. The results are given in Table III below.

TABLE III

| Organism | MIC (µg/ml) Compound | | | | | |
|---|---|---|---|---|---|---|
| | 3.D | 6 | 10 | 11 | 12 | 14 |
| S. aureua 29213 | 0.25,1 | 64,128 | 1 | 0.5,8 | 2,4 | 2,4 |
| E. coli 25922 | 2,4 | >256 | 2,4 | 2,16 | 16 | 16 |
| P. aeruginosa 27853 | 16 | >256 | 4,8 | 8,16 | 16,32 | 64 |
| S. aureus 19564 | N/A | N/A | 2 | N/A | N/A | 1/A |
| S. aureus 10175 | N/A | N/A | 1,2 | N/A | N/A | N/A |
| S. aureus 10185 | N/A | N/A | 2 | N/A | N/A | N/A |
| S. aureus 20846 | N/A | N/A | 2 | N/A | N/A | 1/A |
| S. aureus 20979 | N/A | N/A | 2 | N/A | N/A | N/A |
| S. aureus 6538 | N/A | N/A | 1,2 | N/A | N/A | N/A |
| S. aureus 10164 | N/A | N/A | 1,2 | N/A | N/A | N/A |
| S. aureus 20776 | N/A | N/A | 2 | N/A | N/A | N/A |
| S. aureus 21945 | N/A | N/A | 2 | N/A | N/A | N/A |
| S. aureus 28447 | N/A | N/A | 2 | N/A | N/A | 1/A |
| S. aureus MCP-101 | N/A | N/A | 2 | N/A | N/A | N/A |
| S. aureus KMF | N/A | N/A | 2 | N/A | N/A | N/A |
| S. aureus 1096 | N/A | N/A | 2 | 2 | 4,8 | N/A |
| S. aureus 1093 | N/A | N/A | 2,4 | 2 | 4 | N/A |
| S. epidermidis 12228 | N/A | N/A | 2 | N/A | N/A | N/A |
| S. epidermidis 1050 | N/A | N/A | 2 | 1 | 4 | 1/A |
| S. epidermidis 1090 | N/A | N/A | 2 | 2 | 4 | N/A |
| P. aeruginosa El Salvador | N/A | N/A | 64 | 128 | 256 | N/A |
| P. aeruginosa 1133 | N/A | N/A | 16 | 32 | 128 | N/A |
| P. mirabilis 23147 | 64 | N/A | 256 | >256 | >256 | N/A |
| P. mirabilis 24231 | 64 | N/A | >256 | 7256 | >256 | N/A |
| S. marcescens 18963 | 64 | N/A | >256 | 16 | >256 | N/A |
| S. marcescens 23420 | 64,128 | N/A | >256 | >256 | >256 | N/A |
| E. faecium 26143 | 1 | N/A | 2/4 | 1 | 8 | 8 |
| E. faecalis 19052 | 1,2 | N/A | 16 | N/A | 64 | 64 |
| E. faecalis 19290 | 1,2 | N/A | 16 | 0.5,1 | N/A | N/A |
| E. faecalis 23296 | 2 | N/A | 4 | 1 | N/A | N/A |
| E. faecalis 29212 | 1 | N/A | 4 | 1 | N/A | N/A |
| C. difficile TTU614 | 4 | N/A | 8 | 4 | N/A | N/A |
| C. difficile P324 | 1 | 128 | 1,2 | 2 | 4,8 | N/A |
| B. fragilis 25285 | 2,4 | 256 | 4,8 | 2 | 8 | N/A |
| L. fermentum 23271 | 0.5 | 64 | 1,2 | 1 | 1 | N/A |
| P. gingivalis 381 | 2 | N/A | 8 | N/A | 8 | N/A |
| P. gingivalis FAY-19M-1 | 2 | N/A | 16 | N/A | 32 | N/A |
| P. gingivalis 9-14K-1 | 2 | N/A | 8 | N/A | 16 | N/A |
| P. gingivalis W50 | 4 | N/A | 8 | N/A | 16 | N/A |
| P. gingivalis A7A1-28 | 2 | N/A | 8 | N/A | 16 | N/A |
| P. intermedia 68-9K-3 | N/A | N/A | 1 | N/A | N/A | N/A |
| P. intermedia 25611 | N/A | N/A | 2 | N/A | N/A | N/A |
| P. intermedia 9536 | N/A | N/A | 2 | N/A | N/A | N/A |
| P. intermedia 49046 | N/A | N/A | 1 | N/A | N/A | N/A |
| A. actinomy cetemcomitans 92-1185 | N/A | N/A | 8 | N/A | N/A | N/A |
| A. actinomy cetemcomitans 92-1218 | N/A | N/A | 0.5 | N/A | N/A | N/A |
| A. actinomy cetemcomitans 29522 | N/A | N/A | 4 | N/A | N/A | N/A |
| A. actinomy cetemcomitans 43718 | N/A | N/A | 2 | N/A | N/A | N/A |
| S. mutans 33535 | N/A | N/A | 1 | N/A | N/A | N/A |
| S. mutans 38402 | N/A | N/A | 1 | N/A | N/A | N/A |
| S. mutans 25175 | N/A | N/A | 1 | N/A | N/A | N/A |
| S. sangius 29667 | N/A | N/A | 8 | N/A | N/A | N/A |
| S. sangius 49295 | N/A | N/A | 64 | N/A | N/A | N/A |
| A. viscosus 15987 | N/A | N/A | 2 | N/A | N/A | N/A |
| C. alibicans 14053 | 2,4 | 256 | 16,32 | 2,64 | 32 | 64 |
| C. tropicalis 13803 | 1,2 | N/A | 2 | 2 | N/A | N/A |
| C. tropicalis 28707 | 0.25,0.5 | N/A | 1,2 | 0.5 | N/A | N/A |
| C. parapsilosis 10232 | 2,4 | N/A | 64 | 1,2 | N/A | N/A |
| C. parapsilosis 22709 | 2,4 | N/A | 16 | 1 | N/A | N/A |
| C. kefyr 18838 | 1,2 | N/A | 2 | 1 | N/A | N/A |
| T. mentagrophytes 18748 | 2,16 | N/A | 8 | 4 | 8 | N/A |
| T. rubrum 36262 | 8 | N/A | 8 | 8 | 16 | N/A |
| M. canis 11621 | 4,16 | N/A | 16 | 4 | N/A | N/A |
| R. floccosum 52062 | 4,8 | N/A | 16 | 4 | N/A | N/A |

EXAMPLE 5

Compounds 3, 4, 9, and 36 were prepared as described in Example 1, and tested for minimal inhibitory concentration against various organisms listed in Table IV below according to the assay procedure of Example 2. The results are given in Table IV below.

TABLE IV

| Organism | MIC (µg/ml) Compound | | | |
|---|---|---|---|---|
| | 3 | 4 | 9 | 36 |
| S. aureus 29213 | 1 | 2,4 | 4,8 | 8 |
| E. coli 25922 | 4 | 64,256 | 16,32 | 32 |
| P. aeruginosa 27853 | 4,32 | 128 | 64 | 128 |
| P. mirabilis 23147 | >256 | N/A | >256 | N/A |
| P. mirabilis 24231 | >256 | N/A | >256 | N/A |
| S. marcesens 18963 | 64 | N/A | >256 | N/A |
| S. marcesens 23420 | >256 | N/A | >256 | N/A |
| E. faecium 26143 | 2 | N/A | 8 | N/A |
| E. faecalis 19052 | 1,2 | N/A | 64 | N/A |
| E. faecalis 19290 | 1,2 | N/A | N/A | N/A |
| E. faecalis 23296 | 1,2 | N/A | N/A | N/A |
| E. faecalis 29212 | 1,2 | N/A | N/A | N/A |
| C. difficile TTU614 | N/A | 32 | N/A | N/A |
| C. difficile P324 | N/A | 4 | 8 | N/A |
| B. fragilis 25285 | N/A | 256 | 8 | N/A |
| L. fermentum 23271 | N/A | 4,8 | 2 | N/A |

TABLE IV-continued

| Organism | MIC (µg/ml) Compound | | | |
|---|---|---|---|---|
| | 3 | 4 | 9 | 36 |
| P. gingvalis 381 | 4 | N/A | 8 | N/A |
| P. gingvalis FAY-19M-1 | 4 | N/A | 8 | N/A |
| P. gingvalis 9-14K-1 | 4 | N/A | 16 | N/A |
| P. gingvalis W50 | 4 | N/A | 16 | N/A |
| P. gingvalis A7A1-28 | 4 | N/A | 16 | N/A |
| C. albican 14053 | 4 | 128,256 | 32 | 4,32 |
| C. tropicalis 13083 | 2 | N/A | 4 | 0.5 |
| C. tropicalis 28707 | 0.5 | N/A | 1,2 | ≦0.25 |
| C. parapsilosis 10232 | 2 | N/A | 128 | 0.5 |
| C. parapsilosis 22109 | 2 | N/A | 2,4 | 4 |
| C. kefyr 28838 | 2 | N/A | 2,4 | 4 |
| T. metagro-phytes 18748 | 16 | N/A | 16 | N/A |
| T. rubrum 36262 | 16 | N/A | 16 | N/A |
| M. canis 11621 | 32 | N/A | 64 | N/A |
| E. floccosum 52062 | 16 | N/A | 32 | N/A |

TABLE V

| Organism | MIC (µg/ml) Compound | | | | | |
|---|---|---|---|---|---|---|
| | 19 | 20 | 21 | 22 | 24 | 25 |
| S. aureus 29213 | 4 | 4 | 256 | 8 | 0.5,1 | 1,2 |
| E. coli 25922 | 16 | 16 | 256 | 128 | 16 | 32,64 |
| P. aeruginosa 27853 | 256 | 64 | >256 | 128 | 32,64 | 32,64 |
| C. difficile TTU614 | N/A | N/A | 256 | 32 | 16 | N/A |
| C. difficile P324 | N/A | 8 | 128 | 8,16 | N/A | N/A |
| B. fragilis 25285 | N/A | 16 | 128 | 16,32 | 8 | N/A |
| L. fermentum 23171 | N/A | 2,4 | 64 | 2,4 | 4 | N/A |
| C. albicans 14053 | 32 | 64 | 64,128 | 32 | 256 | 16,32 |
| T. mentagrophytes 18748 | 4 | N/A | N/A | N/A | N/A | N/A |
| T. rubrium 36262 | 16 | N/A | N/A | N/A | N/A | N/A |
| M. Canis 11621 | 32 | N/A | N/A | N/A | N/A | N/A |
| E. floccosum 52062 | 16 | N/A | N/A | N/A | N/A | N/A |

EXAMPLE 6

Compounds 19 through 22, 24, and 25 were prepared as described in Example 1, and tested for minimal inhibitory concentration against various organisms given in Table V below according to the assay procedure of Example 2. The results are given in Table V below.

EXAMPLE 7

Compounds 37–91 were prepared as described in Example 1 and were tested for minimal inhibitory concentration against various organisms listed in Table VI according to the assay procedure given in Example 2. The results are shown in Table VI below.

TABLE VI

| No. | (MSI #) | Name | MIC (µg/ml) | | | |
|---|---|---|---|---|---|---|
| | | | Staph | E. coli | Psuedo | Candida |
| 37 | 107 | β-Guanidino-propionyl dodecylamide | 1 | 4–8 | 16 | 4 |
| 38 | 108 | P-Guanidino-methyl-benzoyl-dodecylamide | 1–2 | 16 | 64 | 4 |
| 39 | 803 | 1,12-[Di-(β-Guanidino propionyl-Arg—Phe)] diaminododecane | 2 | 16 | 64 | 64 |
| 40 | 840 | 1,12-[Di-(Boc-γ-aminobutyryl-Arg—Phe)] diaminododecane | 2 | >256 | >256 | >256 |
| 41 | 841 | 1,12-[Di-(Boc—Ala—Arg—Phe)] diaminododecane | 2 | 32 | >256 | 64 |
| 42 | 844 | 1,12-[Di-(γ-Aminobutyryl-Arg—Phe)] diaminododecane | 4 | 32 | 64 | 64 |
| 43 | 845 | 1,12-[Di-(Ala—Arg—Phe)] diaminododecane | 16 | 128 | 256 | 128 |
| 44 | 869 | 1,12-[Di-(Arg—Arg—Phe)] diaminododecane | 4 | 16 | 64 | 64 |
| 45 | 871 | 1,12-[Di-(Glu—Arg—Phe)] diaminododecane | 256 | 256 | >256 | 64 |
| 46 | 877 | 1,12-[Di-(Phe—Arg)] diaminododecane | 8 | 128 | 128 | 32 |
| 47 | 1219 | 4,4'-[Di-(N$^\alpha$-amidino-Phe)] diaminostilbene | 05–10 | 16 | 32 | 256 |
| 48 | 1220 | 4,4'-[Di-Arg—Phe)] diaminostilbene | 1–2 | 32–64 | 32–64 | 16–32 |
| 49 | 1257 | 4,4'-[Di-Arg] diaminostilbene | 8 | 256 | 128 | 64 |
| 50 | 1237 | H—Arg—Phe—Cys—CONH(CH$_2$)$_{12}$NHCO—Cys—Phe—Arg—H | 64 | 256 | >256 | >256 |
| 51 | 1285 | H—Arg—Phe—Cys(Acm)—CO—NH(CH$_2$)$_{12}$NHCO—Cys(Acm)—Phe—Arg—H | 32 | 64 | 64 | 64 |
| 52 | 1332 | H—Arg—Arg—Phe—Cys(Acm)CO—NH(CH$_2$)$_{12}$NHCO—Cys(Acm)—Phe—Arg—Arg.H | 8 | 16 | 64 | 64 |
| 53 | 1353 | H—Arg—Arg—Phe—Cys—CONH(CH$_2$)NHCO—Cys—Phe—Arg—Arg—Arg—Arg—H | 8 | 16 | 32 | 128 |
| 54 | 1279 | 1,12-[Di-(Arg—Ile)] diaminododecane | 32 | 256 | 256 | 32 |
| 55 | 1284 | 1,12-[Di-(Lys—Phe)] diaminododecane | 128 | >256 | 256 | 64 |
| 56 | 1291 | 1,12-[Di-(Phe—Cha)] diaminododecane (Cha = cyclohexylalamine) | >256 | >256 | >256 | >256 |
| 57 | 1296 | 1,12-[Di-(Arg—Cha)] diaminododecane | 2 | 4 | 8 | 32 |
| 58 | 1308 | 1,12-[Di-(Arg—Phe—Cha)] diaminododecane | 8 | 32 | 256 | 128 |
| 69 | 1311 | 1,12-[Di-(Har—Ile)] diaminododecane (Har = Homoarginine) | 32 | 16 | >256 | 32 |
| 60 | 1313 | 1,12-[Di-(Arg—Tyr)] diaminododecane | 64 | >256 | 256 | 64 |
| 61 | 1340 | 1,12-[Di-(Arg—Ache)] diaminododecane (Ache = 1-amino-cyclohexane-1-carboxylic acid) | 32 | 256 | >256 | 64 |
| 62 | 1341 | 1,12-[Di-(Arg—Leu)] diaminododecane | 32 | 256 | 256 | 32 |

TABLE VI-continued

| | Compound | | MIC (µg/ml) | | | |
|---|---|---|---|---|---|---|
| No. | (MSI #) | Name | Staph | E. coli | Psuedo | Candida |
| 63 | 1342 | 1,12-[Di-(Arg—Nle)] diaminododecane (Nle = Norleucine) | 16 | 64 | 256 | 32 |
| 64 | 895 | $N^\alpha$-Amidino-Arg—Phe—dioctylamide | 2 | 4 | 16 | 16 |
| 65 | 1309 | Arg—Trp-dioctylamide | 2 | 4 | 256 | 16 |
| 66 | 1325 | $N^\alpha$-Amidino-Trp-dioctylamide | 8 | 256 | 256 | 16 |
| 67 | 1345 | $N^\alpha$-Amidino-Phe-dipentylamide | 4 | 64 | 128 | 64 |
| 68 | 1346 | $N^\alpha$-Amidino-Phe-dihexylamide | 0.5–1.0 | 16–32 | 16–64 | 4–16 |
| 69 | 1347 | $N^\alpha$-Amidino-Phe-didecylamide | 128 | 256 | 256 | 64 |
| 70 | 1348 | $N^\alpha$-Amidino-D Phe-dioctylamide | 2 | 64 | 256 | 2 |
| 71 | 1374 | γ-Guanidino-butyryl dioctylamide | 0.5–1.0 | 4 | 32 | <0.25 |
| 72 | 1376 | p-Guanidino methyl-benzoyl dioctylamide | 1 | 4 | 64 | 0.5 |
| 73 | 1378 | $N^\alpha$-Amidino-β-Nal-dioctylamide (β-Nal = β-napthylylalanine) | 4 | >256 | >256 | 4 |
| 74 | 1379 | $N^\alpha$-Amidino-Cha-dioctylamide (cha-cyclohexylalanine) | 2 | >256 | >256 | 2 |
| 75 | 1385 | β-Guanidino-propionyl dioctylamide | 0.5–1.0 | 4–8 | 16 | 1.0 |
| 76 | 1387 | $N^\alpha$-Amidino-Phe-adamantanamide | 16 | 256 | 256 | 128 |
| 77 | 1391 | $N^\alpha$-Amidino-Phe-cyclohexylamide | 128 | >256 | >256 | >256 |
| 78 | 1392 | $N^\alpha$-Amidino-His-dioctylamide | 1 | 4 | 8 | 1 |
| 79 | 1393 | S-Guanidino Valeryl-dioctylamide | 2 | 8 | >256 | 1–2 |
| 80 | 1394 | $N^\alpha$-(Imidazole-2-methyl)-Phe-dioctylamide | 2 | >256 | >256 | >256 |
| 81 | 1395 | Phe-dioctylamide | 4 | >256 | >256 | >256 |
| 82 | 1397 | β-Guanidino-propionyl adamantanamide | 64 | >256 | >256 | >256 |
| 83 | 1399 | $N^\alpha$-Amidino-p-F-Phe-diocytlamide (p-F-Phe = p-fluoro Phenylalanine) | 2–4 | 64 | 128 | 2 |
| 84 | 1402 | γ-Guanidino-β-hydroxy butyrul dioctylamide | 1 | 4 | 16 | 0.5 |
| 85 | 1403 | γ-Guanidino-β-hydroxy butyryl-Phe-dioctylamide | 1 | 32 | 64 | 0.5 |
| 86 | 1406 | $N^\alpha$-Amidino-Glu-(α,γ) diadamantanamide | 4 | 128 | 128 | 32–64 |
| 87 | 1423 | γ-Guanidino-β-hydroxy butyryl-β-Ala-dioctylamide | 2 | 4 | 16 | 0.5 |
| 88 | 1424 | $N^\alpha$-Amidino-p-amino-Phe-dioctylamide | 1 | 4 | 32 | 0.5 |
| 89 | 890 | Arg—Phe-dodecylester | 2–8 | 4–16 | 16 | 8–16 |
| 90 | 891 | β-Ala—Arg—Phe-dodecylester | 4 | 4–8 | 8–16 | 32–64 |
| 91 | 892 | $N^\alpha$-Amidino-Arg—Phe-dodecylester | 4 | 4 | 16 | 32 |

The compounds of the present invention, whether administered alone or in combination with agents such as antibiotics or biologically active peptides or proteins as hereinabove described, may be employed in a wide variety of pharmaceutical compositions in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule or the like. The compound or agent as hereinabove described may also be used in combination with adjuvants, protease inhibitors, or compatible drugs where such a combination is seen to be desirable or advantageous in controlling infection caused by harmful microorganisms including protozoa, viruses, parasites, fungi, and the like.

The compound may be administered to a host in particular an animal, in an effective antibiotic and/or anti-tumor and/or antiviral and/or antimicrobial and/or spermicidal and/or antifungal and/or antiparasitic amount, or in an amount effective to stimulate wound healing in a host. The compounds may be administered either alone or in combination with an antibiotic or ion channel forming peptide or protein as hereinabove described.

When the compound is administered in combination with an agent as hereinabove described, it is possible to administer the compound and agent in separate forms. For example, the agent may be administered systemically and the compound may be administered topically.

When the compound is administered topically, it may be administered in combination with a water-soluble vehicle, said water-soluble vehicle being in the form of an ointment, cream, lotion, paste or the like. Examples of water-soluble vehicles which may be employed include, but are not limited to, glycols, such as polyethylene glycol, hydroxycellulose, and KY Jelly. The water-soluble vehicle is preferably free of an oily substance.

The compounds may also be employed in combination with a ion having pharmacological properties, as hereinabove described, in the form of an oral composition for oral hygiene. Such a composition may be incorporated into a wide variety of compositions and materials used for oral hygiene purposes, which include, but are not limited to, toothpastes, mouthwashes, tooth gels, and tooth powders. Such composition may thus be used to treat or prevent periodontal disease, to prevent or reduce plaque, and/or to prevent or treat or reduce dental caries. The compound and toxic ion may be used to inhibit, prevent, or destroy the growth of *Streptococcus mutants*, which is associated with dental caries and periodontal disease.

Numerous modifications and variations of the present invention are possible in light of the above teachings; therefore, within the scope of the appended claims the invention may be practiced otherwise than as particularly described.

What is claimed is:

1. A compound having the following structural formula:

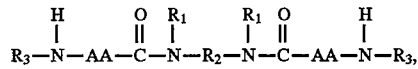

wherein AA is an amino acid or a chain of two or more amino acids, excluding the N-terminus and C-terminus from said amino acid or chain of two or more amino acids;

$R_1$ is hydrogen or an alkyl group having 1 to 8 carbon atoms;

$R_2$ is selected from the group consisting of:
  (i) an aliphatic hydrocarbon having from 1 to about 20 carbon atoms, and

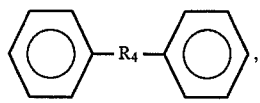 (ii)

wherein $R_4$ is an aliphatic hydrocarbon having 1 to 4 carbon atoms; and $R_3$ is selected from the group consisting of:
  (i) hydrogen; and

 (ii)

wherein $R_5$ is hydrogen or a nitro group.

2. The compound of claim 1 wherein $R_1$ is hydrogen.

3. The compound of claim 1 wherein $R_2$ is an alkyl group having from 7 to 16 carbon atoms.

4. The compound of claim 1 wherein $R_2$ is 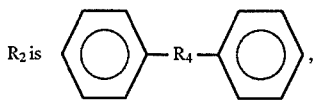, wherein $R_4$ is an aliphatic hydrocarbon having 1 to 4 carbon atoms.

5. The compound of claim 4 wherein $R_4$ is an alkenyl group having from 2 to 4 carbon atoms.

6. The compound of claim 5 wherein $R_4$ is an alkenyl group having 2 carbon atoms.

7. The compound of claim 1 wherein $R_3$ is hydrogen.

8. The compound of claim 1 wherein $R_3$ is:

wherein $R_5$ is hydrogen or nitro.

9. The compound of claim 8 wherein $R_5$ is hydrogen.

10. The compound of claim 8 wherein $R_5$ is nitro.

11. The compound of claim 1 wherein said compound is 1, 12-[di-arginyl-phenylalanyl] diaminododecane.

12. A compound having the following structural formula:

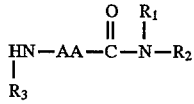

wherein AA is an amino acid or a chain of two or more amino acids, excluding the N-terminus and C-terminus from said amino acid or chain of two or more amino acids;

$R_1$ is hydrogen or an alkyl group having 1 to 8 carbon atoms;

$R_2$ is selected from the group consisting of:
  (i) an aliphatic hydrocarbon having from 7 to 16 carbon atoms, and

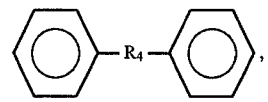 (ii)

wherein $R_4$ is an aliphatic hydrocarbon having 1 to 4 carbon atoms; and $R_3$ is selected from the group consisting of:
  (i) hydrogen; and

 (ii)

wherein $R_5$ is hydrogen or a nitro group.

13. The compound of claim 12 wherein $R_1$ is hydrogen.

14. The compound of claim 12 wherein $R_2$ is an alkyl group having from 7 to 16 carbon atoms.

15. The compound of claim 12 wherein $R_2$ is 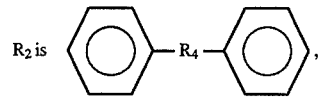, wherein $R_4$ is an aliphatic hydrocarbon having 1 to 4 carbon atoms.

16. The compound of claim 15 wherein $R_4$ is an alkenyl group having from 2 to 4 carbon atoms.

17. The compound of claim 16 wherein $R_4$ is an alkenyl group having 2 carbon atoms.

18. The compound of claim 17 wherein $R_3$ is hydrogen.

19. The compound of claim 12 wherein $R_3$ is:

wherein $R_5$ is hydrogen or nitro.

20. The compound of claim 19 wherein $R_5$ is hydrogen.

21. The compound of claim 12 wherein AA is a phenylalanine residue without the C-terminus and N-terminus.

22. The compound of claim 21 wherein said compound has the following structural formula:

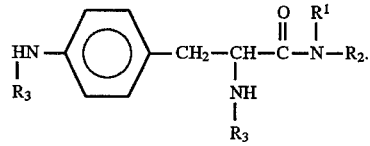

23. The compound of claim 22 wherein $R_3$ is hydrogen.

24. The compound of the claim 22 wherein $R_3$ is:

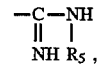

wherein $R_5$ is hydrogen or nitro.

25. The compound of claim 18 wherein $R_5$ is hydrogen.

* * * * *

UNITED STATES PATENT AND TRADEMARK OFFICE
CERTIFICATE OF CORRECTION

PATENT NO. : 5,654,451
DATED : August 5, 1997
INVENTOR(S) : U. Prasad Kari

It is certified that error appears in the above-indentified patent and that said Letters Patent is hereby corrected as shown below:

Claim 22, col. 32, line 45, in the structural formula, "$R^1$" should read --$R_1$--.

Signed and Sealed this

Thirtieth Day of September, 1997

Attest:

BRUCE LEHMAN

Attesting Officer

Commissioner of Patents and Trademarks

US005654451B1

REEXAMINATION CERTIFICATE (3999th)

United States Patent [19]
Kari

[11] B1 5,654,451
[45] Certificate Issued Feb. 22, 2000

[54] AMINO ACIDS AND PEPTIDES HAVING MODIFIED C-TERMINALS AND MODIFIED N-TERMINALS

[75] Inventor: U. Prasad Kari, Lansdale, Pa.

[73] Assignee: Magainin Pharmaceuticals Inc., Plymouth Meeting, Pa.

Reexamination Request:
No. 90/005,048, Jul. 29, 1998

Reexamination Certificate for:
Patent No.: 5,654,451
Issued: Aug. 5, 1997
Appl. No.: 08/430,462
Filed: Apr. 28, 1995

Certificate of Correction issued Sep. 30, 1997.

Related U.S. Application Data

[63] Continuation-in-part of application No. 08/199,553, Feb. 22, 1994, abandoned, which is a continuation-in-part of application No. 08/004,313, Jan. 14, 1993, abandoned.

[51] Int. Cl.[7] .................................................. C07C 233/05
[52] U.S. Cl. .............................. 554/35; 530/300; 554/36; 554/51; 554/53; 564/157; 564/159; 564/164
[58] Field of Search ............................... 554/35, 36, 51, 554/53; 564/153, 157, 159, 164; 530/300; 514/620, 634, 19

[56] References Cited

U.S. PATENT DOCUMENTS

| | | | |
|---|---|---|---|
| Re. 35,224 | 4/1996 | Melmon et al. | 5489/335.5 |
| 3,799,988 | 3/1974 | Hashimoto et al. | 260/561 A |
| 4,202,873 | 5/1980 | Batz et al. | 424/1 |
| 4,468,383 | 8/1984 | Rodbard et al. | 424/177 |
| 4,602,041 | 7/1986 | Newsome et al. | 514/634 |
| 4,647,693 | 3/1987 | Kondo et al. | 562/439 |
| 4,732,916 | 3/1988 | Satoh et al. | 514/620 |
| 4,857,650 | 8/1989 | Iizuka et al. | 548/336 |
| 4,873,253 | 10/1989 | Okamato et al. | 514/352 |
| 4,906,767 | 3/1990 | Mathias et al. | 560/13 |
| 4,912,119 | 3/1990 | Buschauer et al. | 514/333 |
| 4,954,512 | 9/1990 | Oguro et al. | 514/352 |
| 4,990,536 | 2/1991 | Sakasai et al. | 514/563 |
| 5,010,095 | 4/1991 | Sterk et al. | 514/400 |
| 5,037,808 | 8/1991 | Tjoeng et al. | 514/20 |
| 5,145,872 | 9/1992 | Chiarino et al. | 514/620 |
| 5,223,489 | 6/1993 | Hemmi et al. | 514/19 |
| 5,234,917 | 8/1993 | Finkelstein et al. | 514/397 |
| 5,256,645 | 10/1993 | Branca et al. | 514/18 |
| 5,444,080 | 8/1995 | Girard et al. | 514/397 |

FOREIGN PATENT DOCUMENTS

| | | | |
|---|---|---|---|
| 0 175 323 | 9/1985 | European Pat. Off. . | |
| 0394684A1 | 10/1990 | European Pat. Off. . | |
| 0434432A1 | 6/1991 | European Pat. Off. | 564/164 |
| 1 377 806 | 2/1965 | France . | |
| 2015651 | 10/1970 | Germany . | |
| 4636605 | 10/1971 | Japan . | |
| WO 90/05141 | 5/1990 | WIPO . | |

OTHER PUBLICATIONS

Abstract of German patent DE2015651, 1970.

Abstract of Japanese patent 4636605, 1971.

Fuller, A. T., "Antibacterial Action and Chemical Constitution in Long–Chain Aliphatic Bases," *Biochem. J.*, vol. 36, pp. 548–558 (1942).

Murakami, Shohachi, "Preparation of phenylalanine derivaties as inhibitors of acyl–coenzyme A: cholesterol acyltransferase," Chemical Abstracts, vol. 122, No. 11, p. 1190 (Mar. 13, 1995).

Nawrocka–Bolewska, Elenora et al., "Further investigations on the antinociceptive activity of tuftsin analogs," Chemical Abstracts, vol. 117, No. 19, p. 16 (Nov. 9, 1992).

Nicolaides, Ernest, "Potential Antiviral Agents, Carbobenzoxy Di–and Tripeptides Active against Measles and Herpes Viruses," *J. Med. Chem.*, vol. 11, No. 1 pp. 74–79 (1968).

Ono, Mitsunori et al., "Preparation of polypeptide membranes and their supports," *Plastics Fabr., Uses,* Chemical Abstracts, vol. 114, No. 24, p. 69 (Jun. 17, 1991).

Pongracz, Krisztina et al., "Quinoline–and naphthyridine–3–carboxylic acid amides," *Amino Acids, Peptides, Proteins,* Chemical Abstracts, vol. 106, No. 15, p. 681 (Apr. 13, 1987).

Reynolds et al., "1,10–bis(Guanidino) Decane Inhibits N–Methyl–D–Aspartate Responses in Vitro and in Vivo," *The Journal of Pharmacology and Experimental Therapeutics,* vol. 259, No. 2, pp. 626–632 (1991).

Shimohigashi, Yasuyuki et al., "Binding characteristics of a series of dimeric tripeptide enkephalins for δ opiate receptors in rat brains and NG108–15 cells," Chemical Abstracts, vol. 112, No. 23, p. 72 (Jun. 4, 1990).

Taskaeva, Yu M. et al., "Synthesis of tetragastrin analogs substituted in the amide group," *Amino Acids, Peptides, Proteins,* Chemical Abstracts, vol. 117, No. 21, p. 899 (Nov. 23, 1992).

European Search Report, Application No. 94907791.1 (PCT/US94/00335), mailed Mar. 28, 1996.

*Primary Examiner*—Shailendra Kumar

[57]  ABSTRACT

Compounds which have one of the following structural formulae:

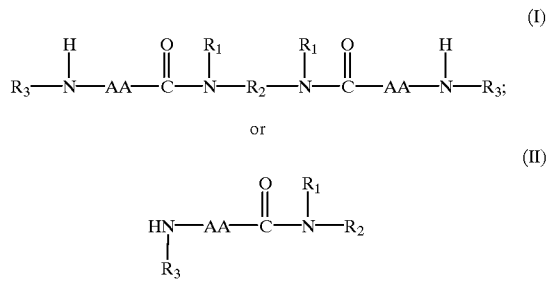

AA is an amino acid residue or an amino acid chain of two or more amino acid residues, excluding the N-terminal and the C-terminal from said amino acid residue or amino acid chain of two or more amino acid residues;

$R_1$ is hydrogen or an alkyl group having from 1 to 8 carbon atoms;

$R_2$ is selected from the group consisting of
(i) a substituted or unsubstituted hydrocarbon having from 1 to 20 carbon atoms, and

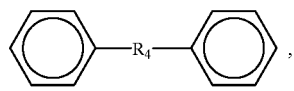

$R_4$ is an aliphatic hydrocarbon having 1 to 4 carbon atoms. $R_4$ may be substituted or unsubstituted.

$R_3$ is selected from the group consisting of
(i) hydrogen;

wherein $R_5$ is hydrogen or a nitro group; and

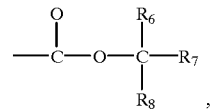

wherein each of $R_6$, $R_7$, and $R_8$ is hydrogen or methyl. The above compounds are useful as pharmaceuticals for inhibiting the growth of target cells, viruses, or virally-infected cells.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 18–19 and 23–24 are cancelled.

Claims 1, 12, 20 and 25 are determined to be patentable as amended.

Claims 2–11, 13–17 and 21–22 dependent on an amended claim, are determined to be patentable.

New claim 26 is added and determined to be patentable.

1. A compound having the following structural formula:

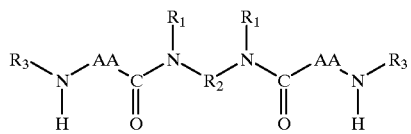

wherein AA is an amino acid, *and when AA is an amino acid, said amino acid is selected from the group of hydrophobic amino acids p-fluorophenylalanine, alanine, Cys, Ile, Leu, Met, Phe, Pro, Trp, Tyr, Val, cyclohexylalanine, norleucine and norvaline; the group of basic hydrophilic amino acids Lys, Arg, His, ornithine, p-aminophenylalanine, 2,4-diaminobutyric acid and homoarginine; and the group of neutral hydrophilic amino acids Asn, Gln, Ser, Thr and homoserine;* or a chain of two or more amino acids, *and when AA is a chain, at least one of the amino acids must be hydrophilic, and only one other amino acid of the chain can contain an aromatic moiety,* excluding the N-terminus and C-terminus from said amino acid or *said* chain [of two or more amino acids];

$R_1$ is hydrogen or an alkyl group having 1 to 8 carbon atoms;

$R_2$ is selected from the group consisting of:
 (i) an aliphatic hydrocarbon having from 1 to about 20 carbon atoms, and

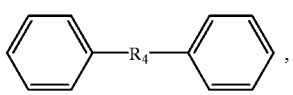

wherein $R_4$ is an aliphatic hydrocarbon having 1 to 4 carbon atoms; and $R_3$ is selected from the group consisting of:
 (i) hydrogen; and

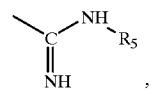

wherein $R_5$ is hydrogen or a nitro group.

12. A compound having the following structural formula:

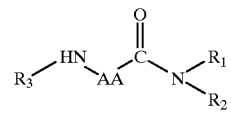

wherein AA is an amino acid or a chain of two or more amino acids, excluding the N-terminus and C-terminus from said amino acid or chain of two or more amino acids;

$R_1$ is hydrogen or an alkyl group having 1 to 8 carbon atoms;

$R_2$ is selected from the group consisting of:
 (i) an aliphatic hydrocarbon having from 7 to about 16 carbon atoms, and

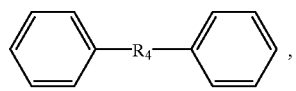

wherein $R_4$ is an aliphatic hydrocarbon having 1 to 4 carbon atoms; and $R_3$ is [selected from the group consisting of:
 (i) hydrogen; and]

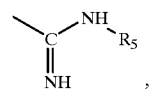

wherein $R_5$ is hydrogen or a nitro group.

20. The compound of claim [19] *12* wherein $R_5$ is hydrogen.

25. The compound of claim [18] *22* wherein $R_5$ is hydrogen.

26. *The compound of claim 1 wherein the hydrophilic amino acid of AA is also charged.*

* * * * *